(12) United States Patent
Yi et al.

(10) Patent No.: US 10,993,672 B2
(45) Date of Patent: May 4, 2021

(54) NON-INVASIVE METHOD AND SYSTEM TO EXTRACT CHARACTERISTIC INFORMATION OF BIO-TISSUES

(71) Applicant: Msheaf Health Management Technologies Limited, Kowloon (HK)

(72) Inventors: Cheng Yi, Marlboro, NJ (US); Peng Xie, Shenzhen (CN); Bixia He, Mao Ming (CN)

(73) Assignee: Msheaf Health Management Technologies Limited, Kowloon (HK)

( * ) Notice: Subject to any disclaimer, the term of this patent is extended or adjusted under 35 U.S.C. 154(b) by 357 days.

(21) Appl. No.: 16/206,863

(22) Filed: Nov. 30, 2018

(65) Prior Publication Data

US 2019/0200933 A1    Jul. 4, 2019

Related U.S. Application Data

(63) Continuation-in-part of application No. 16/004,204, filed on Jun. 8, 2018, now Pat. No. 10,966,668.
(Continued)

(51) Int. Cl.
| | |
|---|---|
| *A61B 5/0205* | (2006.01) |
| *A61B 5/0537* | (2021.01) |
| *A61B 5/0295* | (2006.01) |
| *A61B 5/318* | (2021.01) |
| *A61B 5/00* | (2006.01) |

(52) U.S. Cl.
CPC .......... *A61B 5/7228* (2013.01); *A61B 5/0205* (2013.01); *A61B 5/0537* (2013.01); *A61B 5/4875* (2013.01); *A61B 5/0295* (2013.01); *A61B 5/318* (2021.01)

(58) Field of Classification Search
CPC ....... A61B 5/7278; A61B 5/024; A61B 5/026; A61B 5/0205; A61B 5/7228; A61B 5/7257; A61B 5/0537; A61B 5/7203; A61B 5/4875; A61B 5/0295; A61B 5/318; A61B 2562/0214
See application file for complete search history.

(56) References Cited

U.S. PATENT DOCUMENTS

| | | | |
|---|---|---|---|
| 4,450,527 | A | 5/1984 | Sramek |
| 5,092,339 | A | 3/1992 | Geddes et al. |
| (Continued) | | | |

*Primary Examiner* — Thaddeus B Cox
(74) *Attorney, Agent, or Firm* — Squire Patton Boggs (US) LLP

(57) ABSTRACT

A method and system used to detect characteristic information of internal body tissues applies multiple AC currents of different frequencies simultaneously to a human or animal body. After the modulated voltage signals are received, they are demodulated. Information from both the cardiovascular system and the surrounding tissues is extracted from the carrier waves of specified frequencies. System identification or channel estimation procedures are performed to separate the information from the cardiovascular circulation system and the surrounding tissues. The resistance and capacitance of the cardiovascular system and surrounding tissues are calculated separately. The calculated resistance and capacitance values are used to represent the states of body fluid and cardiovascular circulation. As a result, relevant state information is obtained accurately and reliably to enable accurate measurements of targeted tissues for acquiring health states.

17 Claims, 11 Drawing Sheets

Related U.S. Application Data

(60) Provisional application No. 62/653,596, filed on Apr. 6, 2018, provisional application No. 62/653,610, filed on Apr. 6, 2018, provisional application No. 62/612,442, filed on Dec. 31, 2017.

(56) References Cited

U.S. PATENT DOCUMENTS

| | | | |
|---|---|---|---|
| 5,178,151 | A | 1/1993 | Sackner |
| 5,529,072 | A | 6/1996 | Sramek |
| 8,911,379 | B2 | 12/2014 | Goor et al. |
| 9,332,941 | B2 | 5/2016 | Banet et al. |
| 9,364,158 | B2 | 6/2016 | Banet et al. |
| 9,380,947 | B2 | 7/2016 | Levy et al. |
| 2006/0200033 | A1 | 9/2006 | Keren et al. |
| 2007/0043303 | A1* | 2/2007 | Osypka ............... A61B 5/7239 600/547 |
| 2010/0094175 | A1* | 4/2010 | Hovorka ............ A61G 7/05776 600/587 |
| 2015/0342497 | A1 | 12/2015 | Maktura et al. |
| 2016/0310013 | A1* | 10/2016 | Levy ................... A61B 5/4818 |
| 2018/0143150 | A1 | 5/2018 | Bezemer et al. |
| 2019/0200938 | A1 | 7/2019 | Yi |

* cited by examiner

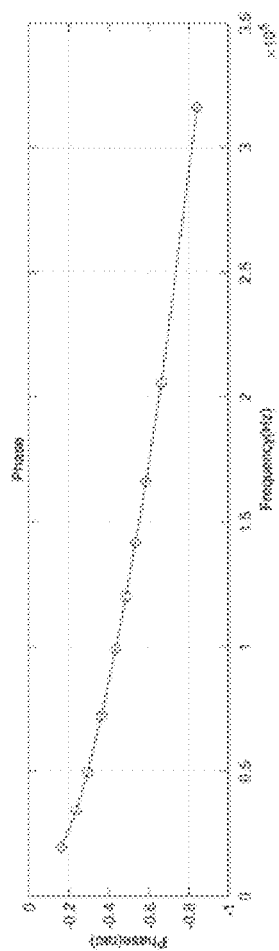
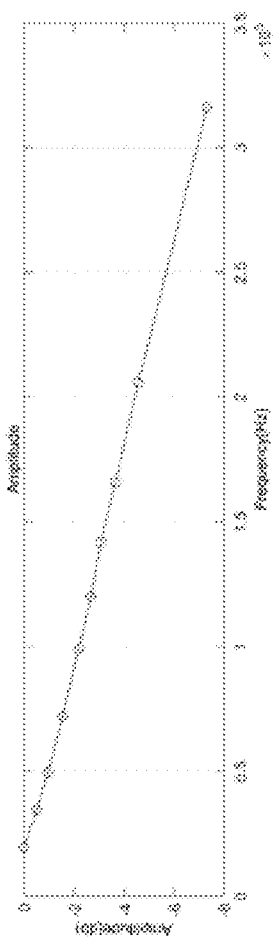
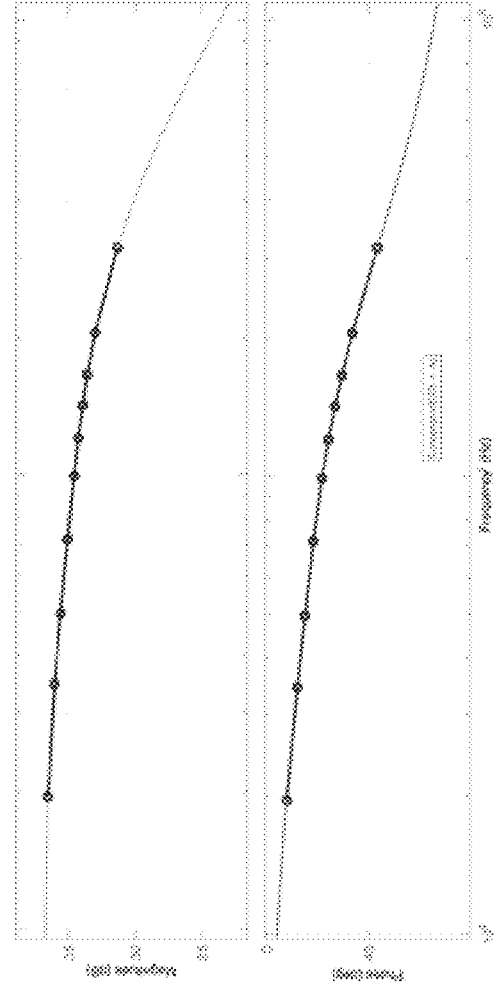
FIG. 6A
FIG. 6B
FIG. 7A
FIG. 7B

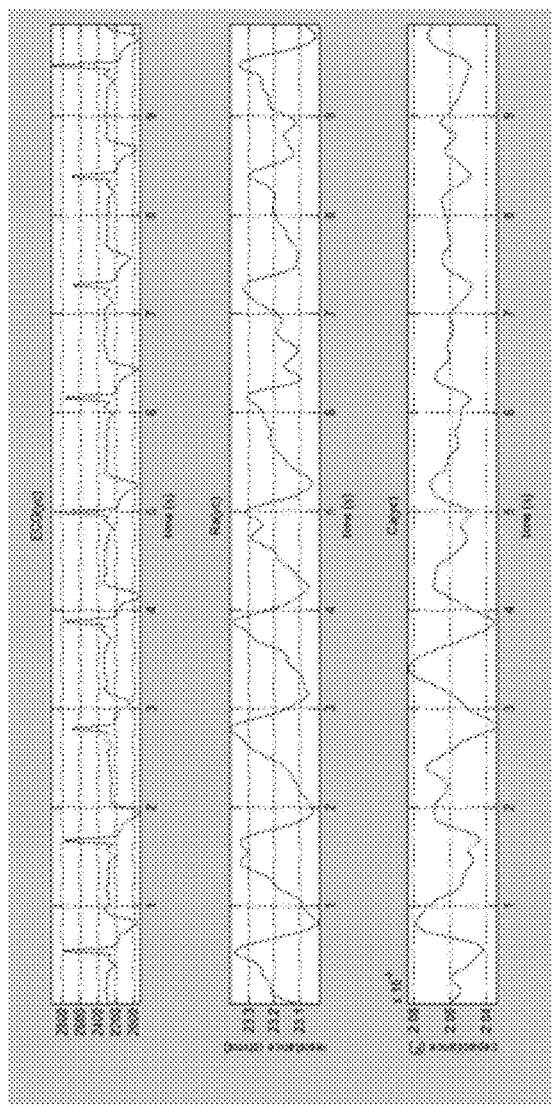
FIG. 8A
FIG. 8B
FIG. 8C
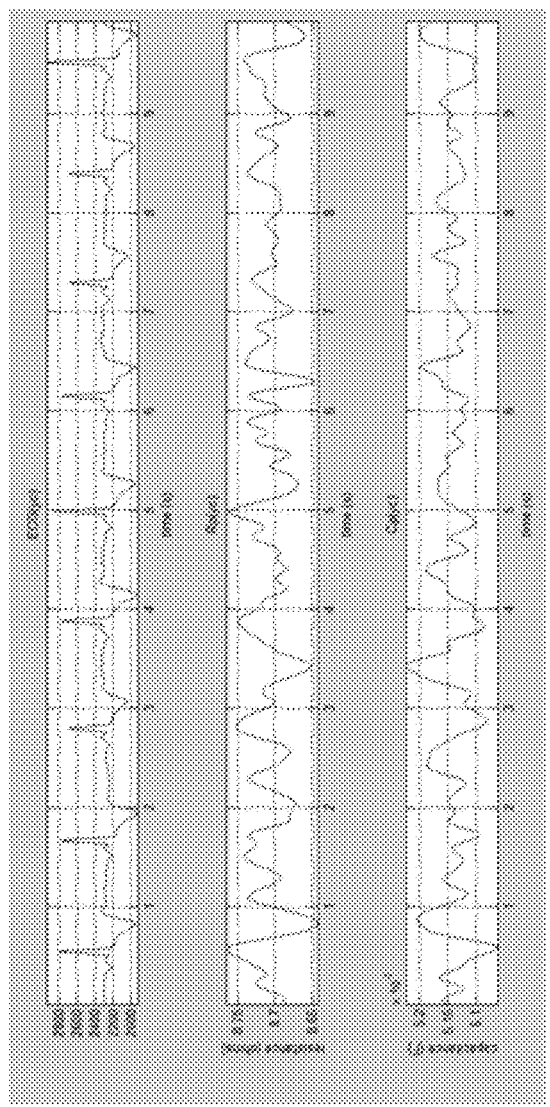
FIG. 9A
FIG. 9B
FIG. 9C

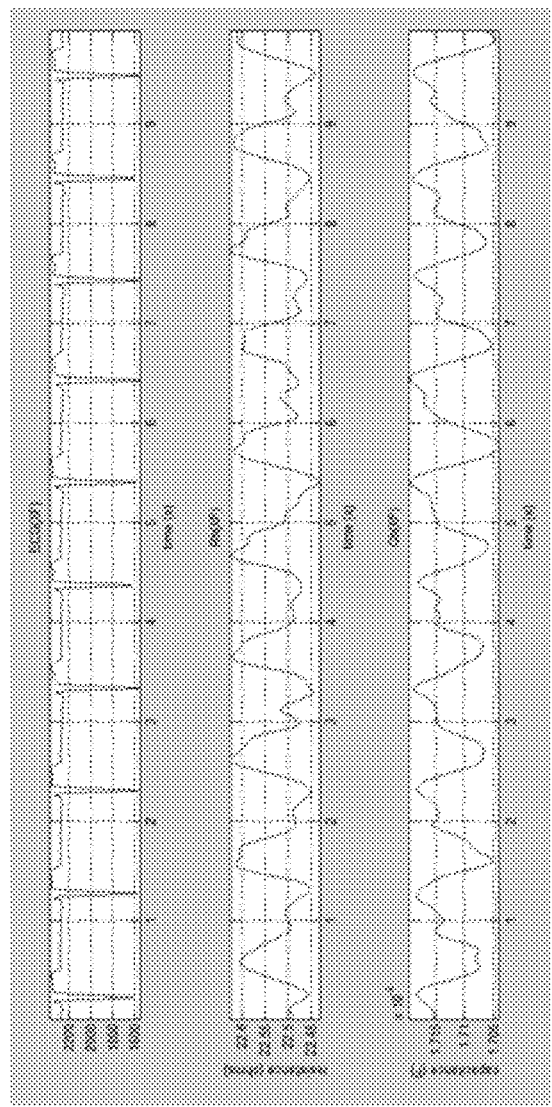
FIG. 10A
FIG. 10B
FIG. 10C
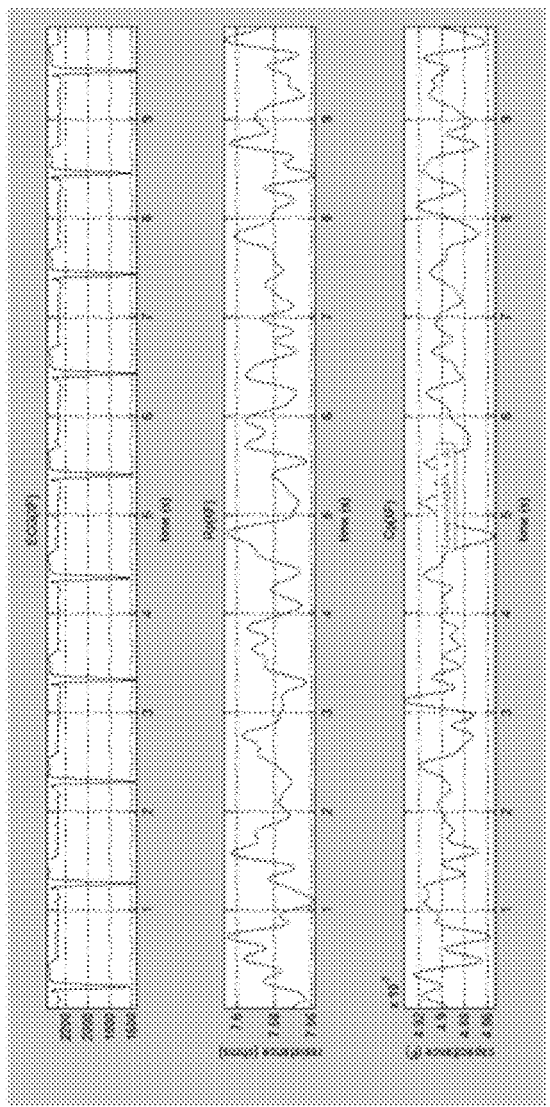
FIG. 11A
FIG. 11B
FIG. 11C

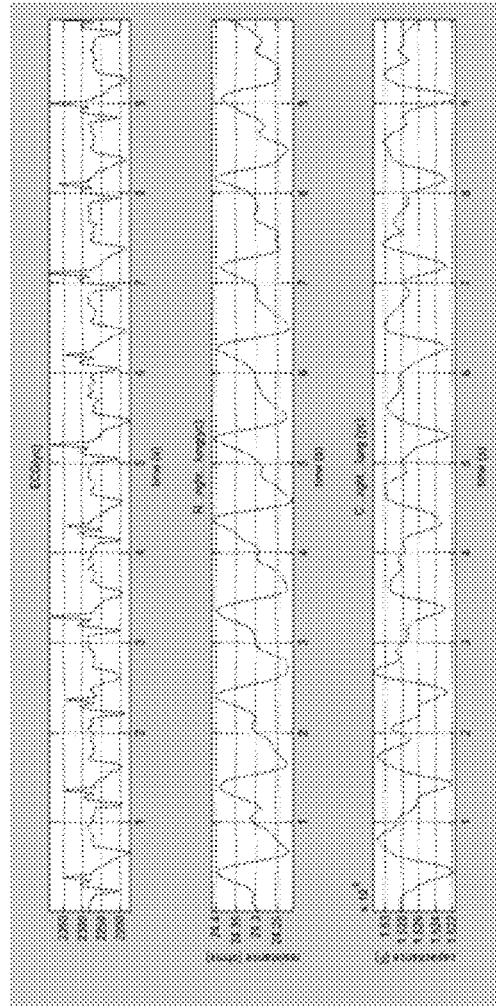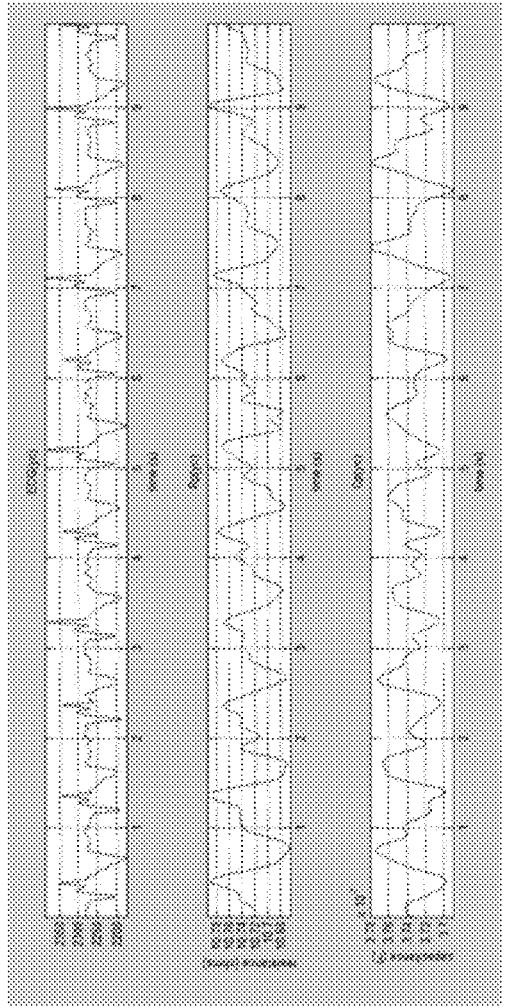
FIG. 14A
FIG. 14B
FIG. 14C
FIG. 15A
FIG. 15B
FIG. 15C

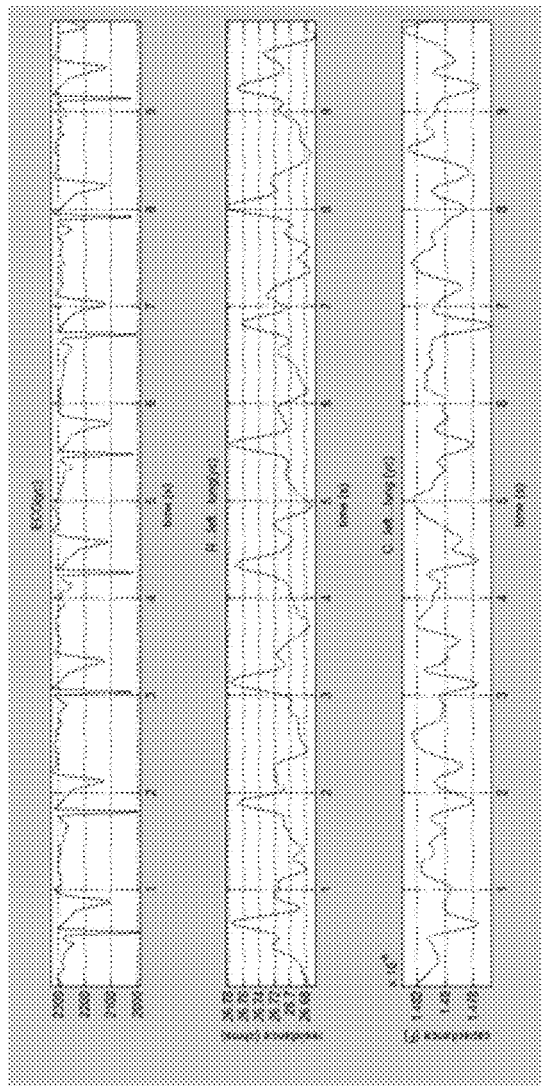
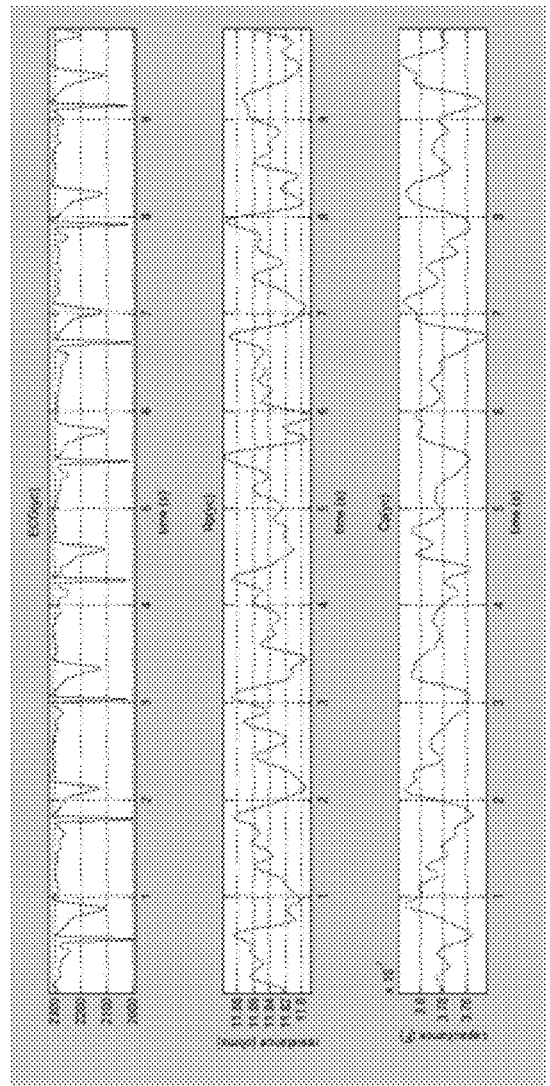

NON-INVASIVE METHOD AND SYSTEM TO EXTRACT CHARACTERISTIC INFORMATION OF BIO-TISSUES

CROSS-REFERENCE TO RELATED APPLICATIONS

The present application is a continuation-in-part of U.S. application Ser. No. 16/004,204, filed Jun. 8, 2018, which claims priority from U.S. Provisional Application No. 62/612,442, filed Dec. 31, 2017. The present application also claims priority from U.S. Provisional Application Nos. 62/653,596 and 62/653,610, both filed Apr. 6, 2018. All of these just-referenced applications are incorporated herein by reference in their entirety.

FIELD OF THE INVENTION

The present invention relates to a non-invasive method and system to extract characteristic information of internal body tissues.

BACKGROUND OF THE INVENTION

Bio-Impedance and bio-reactance measurements as a non-invasive method to measure blood flow and body fluid levels have been explored widely. These technologies are well accepted in the medical field. But the technologies suffer some drawbacks. First, all the computed parameters are based on impedance, which is frequency dependent. These parameters can only indirectly represent the cardiovascular states. Also, since the parameters are frequency dependent, they will suffer frequency-selective impairment. Second, the connecting tissues' impedance plays a big role in the impedance measurements. Traditional bio-impedance and bio-reactance measurements suffer from the mixture of impedance from the targeted area and from the targeted area's surrounding tissues. Sometimes it can be difficult to determine which impedance dominates. Therefore, the mixed impedance varies for different people; even for the same person, the mixed impedance can vary for different tissue states. Therefore, bio-impedance and reactance are not good candidates to represent the characteristics of body fluid and cardiovascular circulation.

Bio-tissues are characterized as conductors and non-conductors from the electrical perspective. Conductors are measured by the conductance (inverse of resistance), while non-conductors can be measured by the capacitance or permittivity. One widely approved human or animal tissue model is the Cole Model. Basically, the AC current is mainly conducted by the extracellular liquid which is mainly resistance at low frequencies, such as 1 KHz. As the AC current's frequency increases, the AC current passes through both extracellular fluid and cells. Since cells have membranes which behave like capacitors, the AC voltage will have phase change. As the frequency keeps increasing, beyond 1 MHz, the cells' membrane effects in the total impedance become insignificant, and the total impedance becomes like a pure resistor again. The Cole Model describes this behavior.

Any bio-tissue's change will basically cause changes in their conductance and capacitance. Therefore, to represent the tissues' changes, the measurement of changes of tissues' conductance and capacitance is far more reliable than the measurement of bio-impedance mixed with bio-reactance, which include the connecting tissues' impedance and reactance. Since the tissues' conductance and capacitance are frequency-dependent, a frequency band has to be chosen. It has been widely accepted that the tissue's information is mainly in a 10 KHz to 1 MHz band. Accordingly, to measure the tissues' conductance and capacitance, multi-frequency alternating stimuli (electrical currents) in the 10 KHz to 1 MHz band may be used. From Ohm's Law, the tissues' conductance and capacitance can be computed from the multiple-frequency alternating electrical currents.

SUMMARY OF THE INVENTION

Embodiments of the present invention overcome the deficiencies of the prior art and provide a non-invasive method to detect electrical characteristics of bio-tissues, which targets capturing the bodily fluid changes, blood flow and the variations of cardiovascular circulations to achieve accurate detection of characteristic information of the targeted tissues, and further to obtain the states of the human or animal body. The method is mainly used for information detection for non-treatment purposes.

Embodiments provide a non-invasive method and system to detect characteristic information of internal body tissues, to capture changes of bodily fluid, blood flow and/or cardiovascular circulations, the method comprising:
generating multiple alternating currents of different frequencies simultaneously;
transmitting the generated multiple alternating currents into a human or animal body to produce multiple alternating voltage signals;
receiving the alternating voltage signals modulated by tissues' changes in the human or animal body;
amplifying and digitizing the received alternating voltage signals into digital signals;
pre-processing the digital signals, the pre-processing further comprising demodulating, filtering, and separating the digital signals;
calculating resistance and capacitance values from the digital signals; and
estimating states of targeted tissues.

In an embodiment, multiple alternating currents of different frequencies are generated from the frequency domain to the time domain using digital signal processing technologies, and the multiple alternating currents of different frequencies are periodic.

In an embodiment, the period of transmitted alternating currents is determined and the received signals are synchronized every period.

In an embodiment, the resistance and capacitance values of the targeted tissues and the peripheral tissues are calculated through system identification or channel estimation procedures.

In an embodiment, multi-chamber modeling is performed using the resistance and capacitance values, and each chamber consists of a parallel resistance and capacitance, and multiple chambers are connected serially, or in parallel, or a mixture of serial and parallel.

In an embodiment, the multi-chamber modeling can be two-chamber modeling, and connecting tissues are between electrodes and the targeted tissues.

In an embodiment, the frequency range is from 10 KHz to 1 MHz.

A system for implementing any of the foresaid methods comprises terminal, one or more math accelerators and one or more processors, wherein the terminal comprises:
a generator for generating multiple alternating currents of different frequencies;

at least one electrical transducer to transfer the generated currents into a human body or animal body, and receiving the alternating voltage signals modulated by the tissues' changes in the human or animal body;

at least one amplifier to amplify the received alternating voltage signals as amplified signals, and at least one analog to digital converter to digitize the amplified signals into digital signals;

a pre-processing module for pre-processing the digital signals, the pre-processing further comprising demodulating, filtering, separating the digital signals;

wherein the at least one math accelerator is configured to calculate resistance and capacitance values from the digital signals; and the at least one processor is configured to estimate states of targeted tissues.

In an embodiment, at least one math accelerator is configured to calculate resistance and capacitance values from the digital signals.

In an embodiment, the at least one processor is remote to remotely watch the system working in real-time.

In an embodiment, the system may connect to outside terminals, such as remote computers, to enable remote monitoring of system operation in real-time.

In an embodiment, the system is configured to operate in an offline mode and enable observation of previously-obtained results.

In an embodiment, the terminal comprises a human interface to operate the system and/or show results.

Aspects of the present invention relate to a method and system to detect characteristics of bio-tissues. Multiple AC currents of different frequencies are applied simultaneously to an animal or human body. After the modulated voltage signals though the body are received, the received signals are demodulated. The information from both the cardiovascular system and the surrounding tissues is extracted from carriers which have specified frequencies. System identification or channel estimation procedures are performed to separate the information from cardiovascular circulation system and the surrounding tissues. The resistance and capacitance of the cardiovascular system and of the surrounding tissue are calculated, separately, using the computed resistance and capacitance to represent the states of body fluid and cardiovascular circulation. As a result, the related information can be obtained accurately and reliably to detect the targeted tissues.

BRIEF DESCRIPTION OF THE DRAWINGS

Embodiments according to the present invention will be described below in detail conjunction with the accompanying drawings, in which:

FIGS. 6A and 6B are graphs of a human or animal frequency response according to an embodiment;

FIGS. 7A and 7B are graphs of a human or animal frequency response against a 2-order RC human or animal model according to an embodiment;

FIGS. 8A-8C are graphs of artery results from a two-chamber model on the aorta measurement according to an embodiment;

FIGS. 9A-9C are graphs of peripheral results from a two-chamber model on the aorta measurement according to an embodiment;

FIGS. 10A-10C are graphs of heart results from a two-chamber model on the heart measurement according to an embodiment;

FIGS. 11A-11C are graphs of peripheral results from a two-chamber model on the heart measurement according to an embodiment;

FIGS. 14A-14C are graphs of artery/vein results from a two-chamber model on the right lung measurement according to an embodiment;

FIGS. 15A-15C are graphs of peripheral results from a two-chamber model on the right lung measurement according to an embodiment;

FIGS. 16A-16C are graphs of artery/vein results from a two-chamber model on the left lung measurement according to an embodiment;

FIGS. 17A-17C are graphs of peripheral results from a two-chamber model on the left lung measurement according to an embodiment.

DETAILED DESCRIPTION OF EMBODIMENTS

Figure 1:
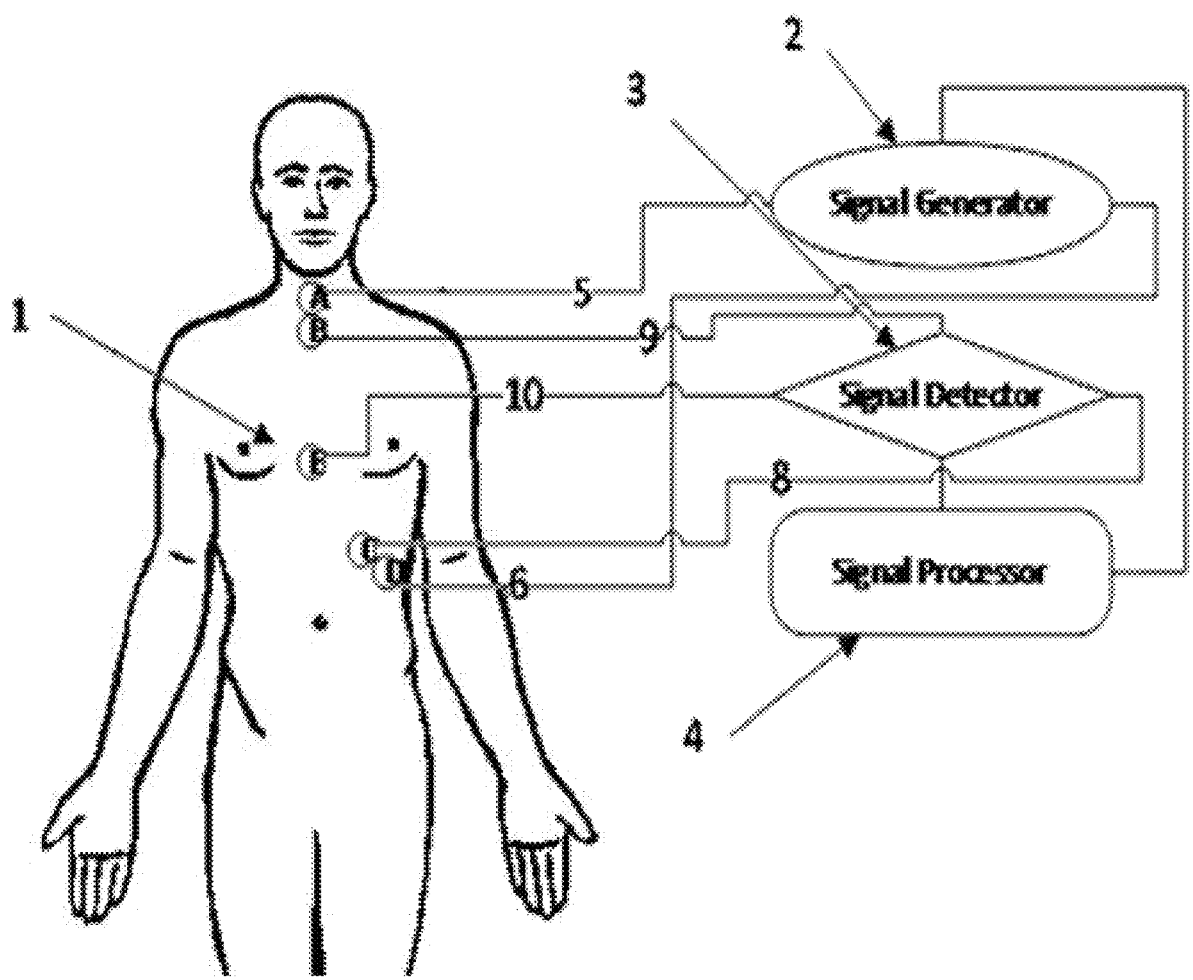
FIG. 1 is a high-level overview of a portion of the system according to an embodiment.

Embodiments of the invention will now be described in further detail with reference to the drawings.

The present invention is related to non-invasive technologies to detect electrical characteristics of bio-tissues, such as tissues' resistance and capacitance and their patterns of change. Embodiments of the invention are directed to capturing body fluid changes, blood flow, and variations of cardiovascular circulation for monitor and information detection for non-treatment purposes. In one aspect, multiple AC currents of different frequencies are supplied simultaneously to a human or animal body. After the modulated voltage signals are received, they are demodulated. Information regarding both the cardiovascular system and surrounding tissue is extracted from carriers at specified frequencies. System identification or channel estimation procedures are performed to separate different information from cardiovascular circulation system and the surrounding tissues. Resistance and capacitance for the cardiovascular system and the surrounding tissues are calculated separately, and are used to represent the states of body fluid and cardiovascular circulation.

In this manner, aspects of the present invention enable monitoring the hemodynamics of a human or animal, including body fluid and blood flow, the states of arteries, heart and lungs, extracting the tissues' resistance and capacitance variations to obtain the quantitative correlations between cardiovascular circulations, body fluid and states of cardiovascular tissues (including heart and lungs).

Multiple alternating electrical currents (AC) of different frequencies are generated from the frequency domain to the time domain using digital signal processing technologies. The multiple alternating currents of different frequencies are periodic.

The period of transmitted signals is determined and the received signals are synchronized every period.

The peripheral tissues' resistance and capacitance are separated from the targeted cardiovascular tissues' resistance and capacitance derived from complex impedance of multiple frequencies.

The information from both the cardiovascular system and the surrounding tissues is extracted from carriers at specified frequencies and is separated through system identification or channel estimation procedures.

Aspects of the present invention provide a method to detect changes of amplitudes and phases of the multiple alternating voltages of different frequencies, or the real and imaginary parts of complex voltage simultaneously. The changes of amplitudes and phases of the multiple alternating electrical currents are translated into resistances and capacitances of internal body tissues.

After the signal processing, the demodulated signals are filtered and processed to perform multi-chamber modeling, and the information about the cardiovascular system is separated from the information for surrounding tissues by using multi-chamber modeling.

Multiple alternating currents of different frequencies are provided simultaneously into a human or animal body through electrodes and form a loop with some external electrical parts. When the electrical currents are traveling in a human or animal body, they are modulated by the body tissues and the tissues' changes in the loop. There are receiving loops which partially overlap with the injecting loop, where the modulated alternating currents can be detected and sampled. The sampled modulated signals and electrocardiographic (ECG) signals will be amplified and digitized into a digital format, to be processed by computers. After the signal processing, the demodulated data from the signals of multiple frequencies are filtered and processed to perform multi-chamber modeling.

A two-chamber RC (resistance and capacitance) model is used to model the targeted tissue. Multiple chambers can be used to model the human or animal bodies. For example, for thorax measurement, one chamber can represent arteries, atria and ventricles, which constitute the main part of the cardiovascular circulation system. The other chamber can represent the connecting tissues between the electrodes and the cardiovascular circulation system. Each chamber may be represented by a parallel RC network comprising integrated resistance and capacitance. The two chambers may be serially connected because the artery systems are not directly connected on the electrodes. The connecting tissues are always between the measuring electrodes and arteries. The system identification or channel estimation technologies are used to calculate the integrated R (resistance) and C (capacitance) values. The R and C values are used to estimate the body fluid, blood flow and cardiovascular circulations. The advantage of the two-chamber model is to enable separation of the cardiovascular circulation system from the surrounding tissues. There also is a three-chamber model which is based on a two-chamber model, which is a parallel RC network (Rc and Cc) parallel to another parallel RC network which is constituted by two serially-connected parallel RC networks (parallel RC network Rp and Cp serially connected to parallel RC network Ri and Ci), as seen for example in FIG. 4. The three-chamber model is more adaptable to human or animal body tissues, but requires more computations, and is less stable.

The tissue RC values are frequency-independent from a narrow-frequency band perspective, for example, 10 KHz to 1 MHz. By combining the changes of the two-chamber's resistance and capacitance with the electrocardiograph (ECG) timing reference, the cardiovascular states can be estimated. The present invention provides technologies to measure the integrated R and C values of this two-chamber model. Multiple chamber models can be processed similarly. The present invention provides 10 frequency responses at a rate of 751 Hz to perform the two-chamber model measurement. These 10 frequency responses are from the demodulation of received signals, and are used to estimate the integrated R and C values. As a result, the two-chamber R and C values are estimated 751 times per second, which is high enough to show the cardiovascular changes. More frequency responses can be used, but more computations would be required.

Aspects of the present invention provide a system to implement any of the above-described methods, wherein the system comprises a terminal, at least one math accelerator, and at least one processor, wherein the terminal comprises:

a generator to generate multiple alternating currents of different frequencies;

One or more electrical transducers to transfer the generated currents into a human body or animal body, and to receive the alternating voltage signals modulated by tissues' changes in the human or animal body;

One or more receiving amplifiers to amplify and digitize the received alternating voltage signals into digital signals;

A pre-processing module to pre-process the digital signals, the pre-processing further comprising demodulating, filtering, and separating the digital signals;

wherein the at least one math accelerator is configured to calculate resistance and capacitance values from the digital signals; and the at least one processor is configured to estimate states of targeted tissues.

The processor can be a single computer or a plurality of computers with or without an array of math accelerators. Ordinarily skilled artisans understand math accelerators to be dedicated circuitry to handle calculations by offloading them from processors which may handle many tasks in a terminal or system.

The terminal further may be constituted by interfaces to connect a human to the system. The computer or computers can be remote, so that human (doctors) can remotely watch the system in real-time.

In one aspect, embodiments of the present invention provide a method and system to examine correlations between changes of internal body resistances and capacitances and body fluid and cardiovascular circulation.

Aspects of the present invention provide a method and system to extract characteristic information from resistances and capacitances of internal body tissues to represent the human or animal hemodynamics and body fluid states, using values which include, but are not limited to a slope of resistance and capacitance curves, a slope of a first derivative of such curves, time periods, normalized amplitude changes, integrated shape areas, or ratios of different states (e.g. systole and diastole for cardio-states).

Aspects of the present invention provide a method and system to relate the computed targeted tissues' resistance and capacitance changes to the arterial elasticities. Therefore, the computed human or animal arterial models can match the measured RC characteristic models.

Aspects of the present invention provide a method and system to relate the computed targeted tissues' resistance and capacitance changes to the myocardial tissues' states. Therefore, the computed human or animal heart mechanical models can match the measured RC characteristic models.

Aspects of the present invention provide a method and system to change the number of frequencies and the frequency values, the timings or phases, and the intensities of AC currents.

Aspects of the present invention provide a method and system to use some or all of the above information to evaluate health states of cardiovascular circulation, including body fluid states.

The foregoing techniques, which will be described in more detail below, enable accurate measurement of targeted tissues, with improved measurement accuracy.

Embodiments of the present invention now will be described in more detail as follows, with reference to the drawings.

FIG. 1 shows a set-up of a terminal system according to an embodiment. A human or animal subject 1 has electrodes or contacts A, B, C, D, and E connecting the system. A signal generator 2 generates a wide frequency-band signal composed of multi-frequency components, from 10 KHz to 1 MHz. The signal generator 2 is connected to electrodes or contacts A and D through wires or cables 5 and 6. Electrodes or contacts A and D are selected so that the generated or stimulating signals can pass through the related arteries, lungs and heart, in this case the thorax, through which several major arteries pass. The signal flow follows the blood flow or the arteries' longitudinal directions. The generated signals travel inside through the human or animal subject from A to D, or from D to A.

Signal detector 3 collects voltage signals from locations B and C, B and E, and E and C through wires or cables 8, 9 and 10. E is a special electrode, which can be one or a pair of electrodes performing transmission and reception at the same time. Signal processor 4 controls and coordinates signal generator 2 and signal detector 3. Signal processor 4 also processes the collected signals from B, C and E, and extracts the bio-information from those locations.

Figure 2:
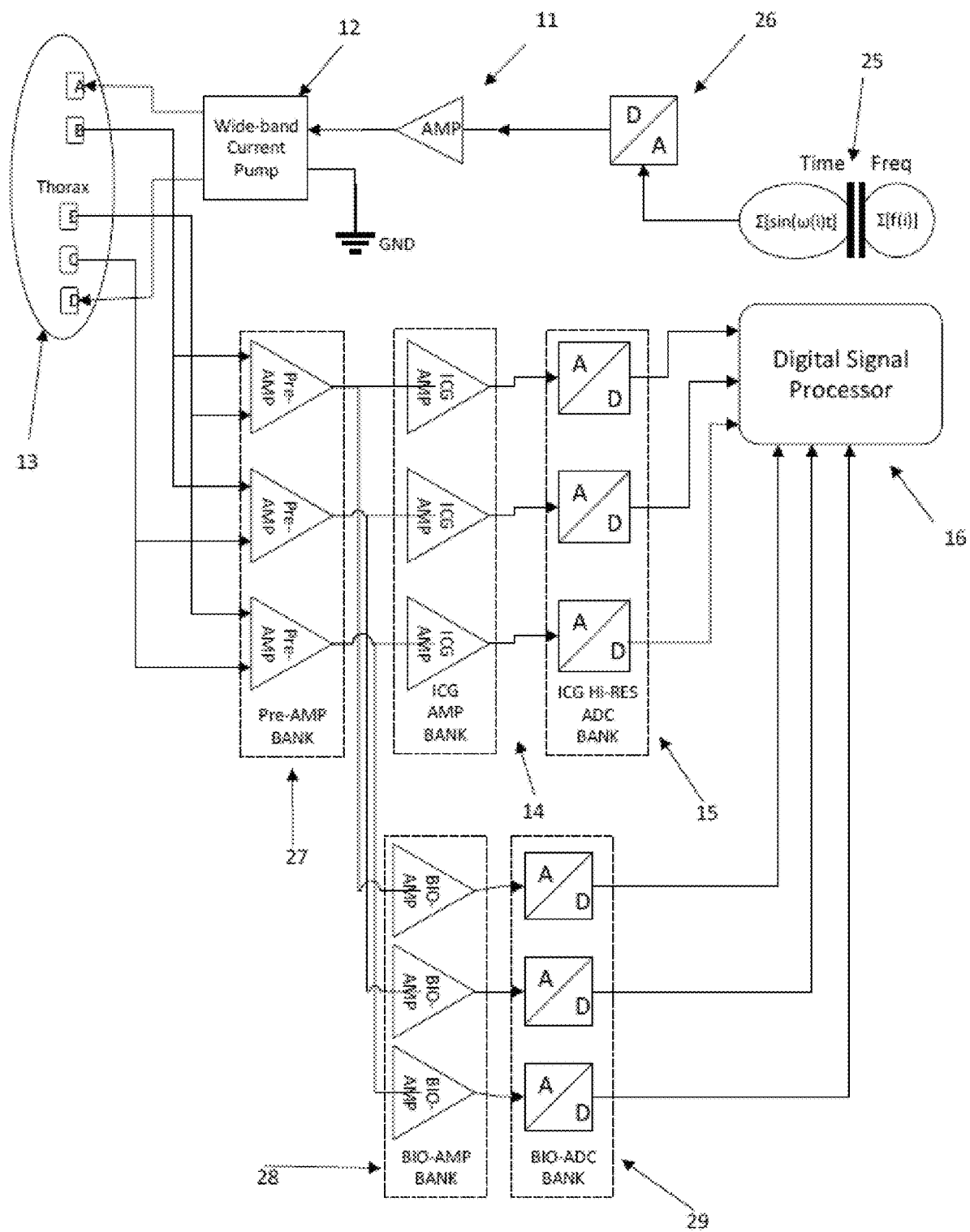
FIG. 2 is a more detailed view of a portion of the system, according to an embodiment.

FIG. 2 shows a functional view or the structure of the terminal system, also called the acquisition system. In this case, the system not only acquires the signals, but also sends the stimulating currents into the human or animal body and tissues. Signal generator 25 works both in the time domain and the frequency domain, and generates the multi-frequency signals. In the time domain these signals are the summation of multiple sine or cosine waves. In the frequency domain they are the summation of multiple frequency tones. Signal generator 25 transforms the frequency tones into multiple sinusoidal signals in the time domain. The generated digital sinusoidal signals pass through a digital-to-analog converter 26, and become analog signals. These analog signals in turn pass through analog amplifier 11 and get amplified to drive a wide frequency-band current pumper device 12 to output a wide band electrical current. From the current pumper device 12, a small current of multiple-frequency sinusoidal waves enters the human or animal body via contacts or electrodes A and D. The human or animal body, which is a complex medium, will modulate the travelling electrical voltage. The modulated voltage and other bio-electrical signals will be picked up from locations B and C, B and E, and E and C. Since all of these signals are weak, they will be amplified by an analog pre-amplifier bank 27 which is mainly used to transform input signals of high impedance into input signals of low impedance.

There are two signal paths from each of the pre-amplifiers in pre-amplifier bank 27. One of these signal paths goes into one of a bank of impedance cardiogram (ICG) amplifiers. The other signal path goes into one of a bank of bio-signal amplifiers. ICG signals and bio-signals need different gains and filters. In general, ICG signals go into ICG amplifier bank 14. Bio-signals go into bio-signal amplifier bank 28. After being amplified, ICG signals are digitized by "IGC Hi-RES ADC BANK" 15, which is a bank of high-resolution and high-speed analog to digital converters. Digital signal processor 16 processes the digitized signals, performing various preprocessing such as demodulation, filtering, extraction of different bio-signals, and the like.

Figure 3:
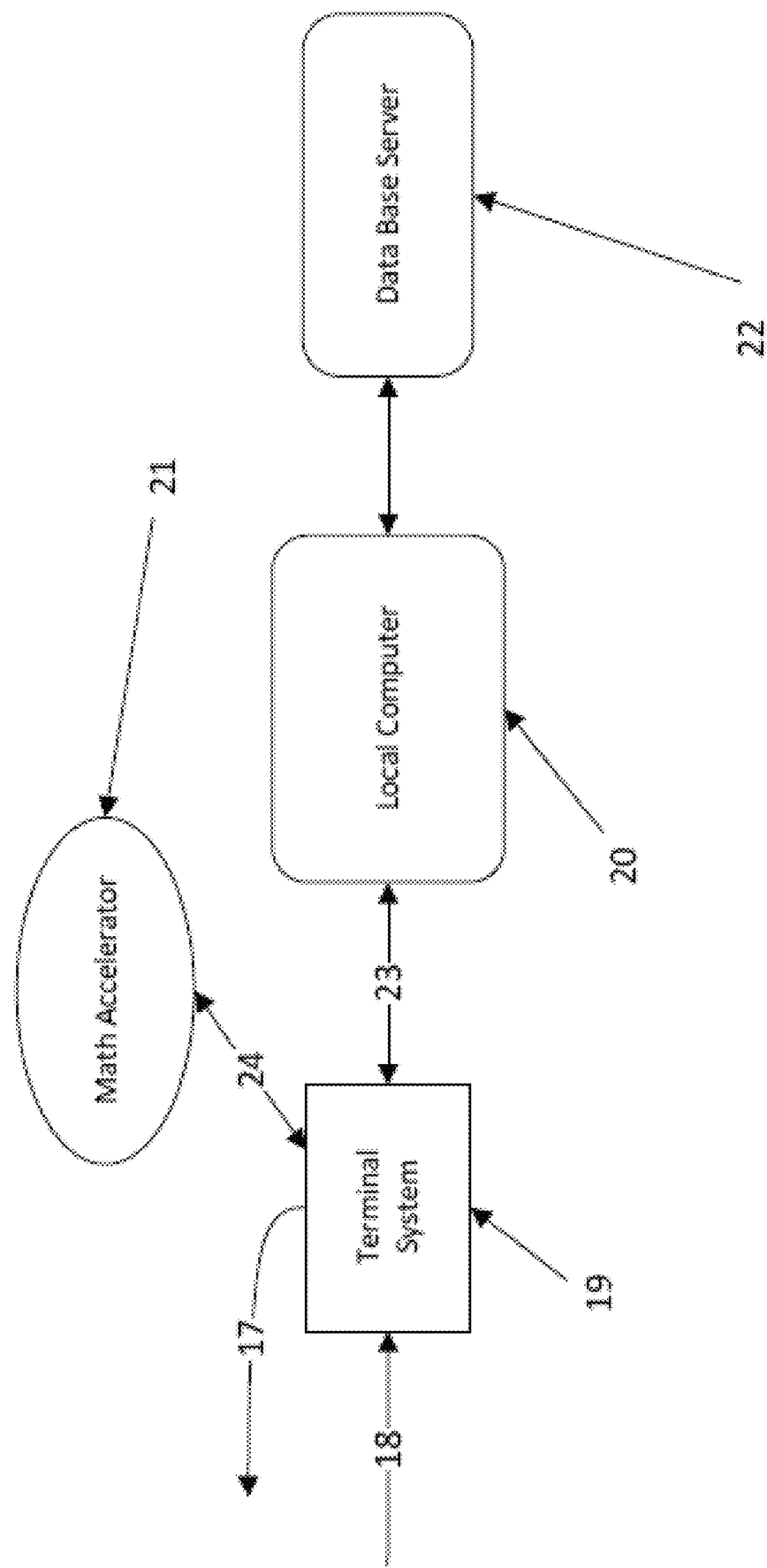
FIG. 3 is a high-level diagram of another portion of the system, according to an embodiment.

FIG. 3 shows how the computer systems work according to embodiments. Stimulating signals go out over path 17. Modulated signals and other bio-signals from a human or animal body come in over path 18. Terminal system 19 does some pre-processing work, including but not limited to demodulation and filtering. Terminal system 19 also can also have its own human or animal interface.

In one embodiment, terminal system 19 is connected to a math accelerator 21 over path 24. Math accelerator 21 performs the computation of system identification or channel estimation to get RC model values, and sends out the intermediate results to local computer 20, where all the final processing, such as parameter calculations, feature extractions, and data analyses, are done. A database server 22, which may be either local computer storage servers or remote computer storage servers, such as cloud-based computer storage servers, stores the results and the data. Database server 22 also may be a mix of both local and remote computer storage servers.

Figure 4:
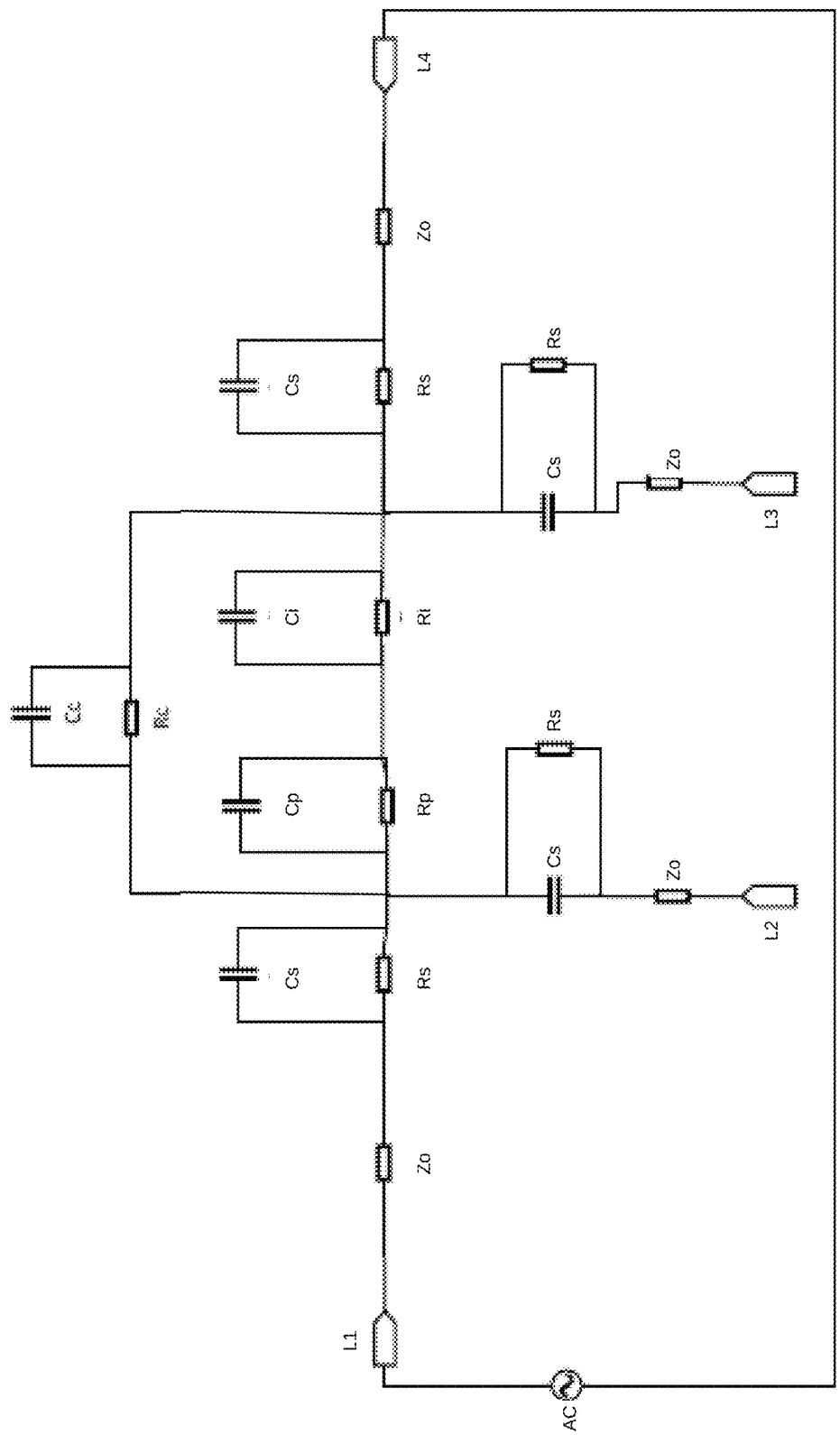
FIG. 4 is a diagram of multi-chamber model measurement circuitry according to an embodiment.

FIG. 4 is a diagram depicting circuitry that models a multi-chamber. FIG. 4 shows three chambers, represented by Rc and Cc, Rp and Cp, and Ri and Ci. FIG. 4 includes a multi-frequency AC current source AC with an intensity I, driving leads L1 and L4 which contact a subject, and receiving leads L2 and L3 which also contact the subject. Cs is the skin capacitance of the subject, and Rs is the skin resistance of the subject. Resistance-capacitance (RC) pairs Cp-Rp (for peripheral or connecting tissues), Cc-Rc (for the direct tissue connection between two receiving leads parallel to the cardiovascular system), and Ci-Ri (for the circulatory system or tissue of interest) together constitute a human or animal tissue RC model. For a simplified two chamber model, Rc and Cc may be dropped. For the two chamber model, two parallel RC pairs Rp-Cp and Ri-Ci are connected serially. The three chamber RC model, which yields a more realistic model, requires more computations, and is less stable.

Figure 5:
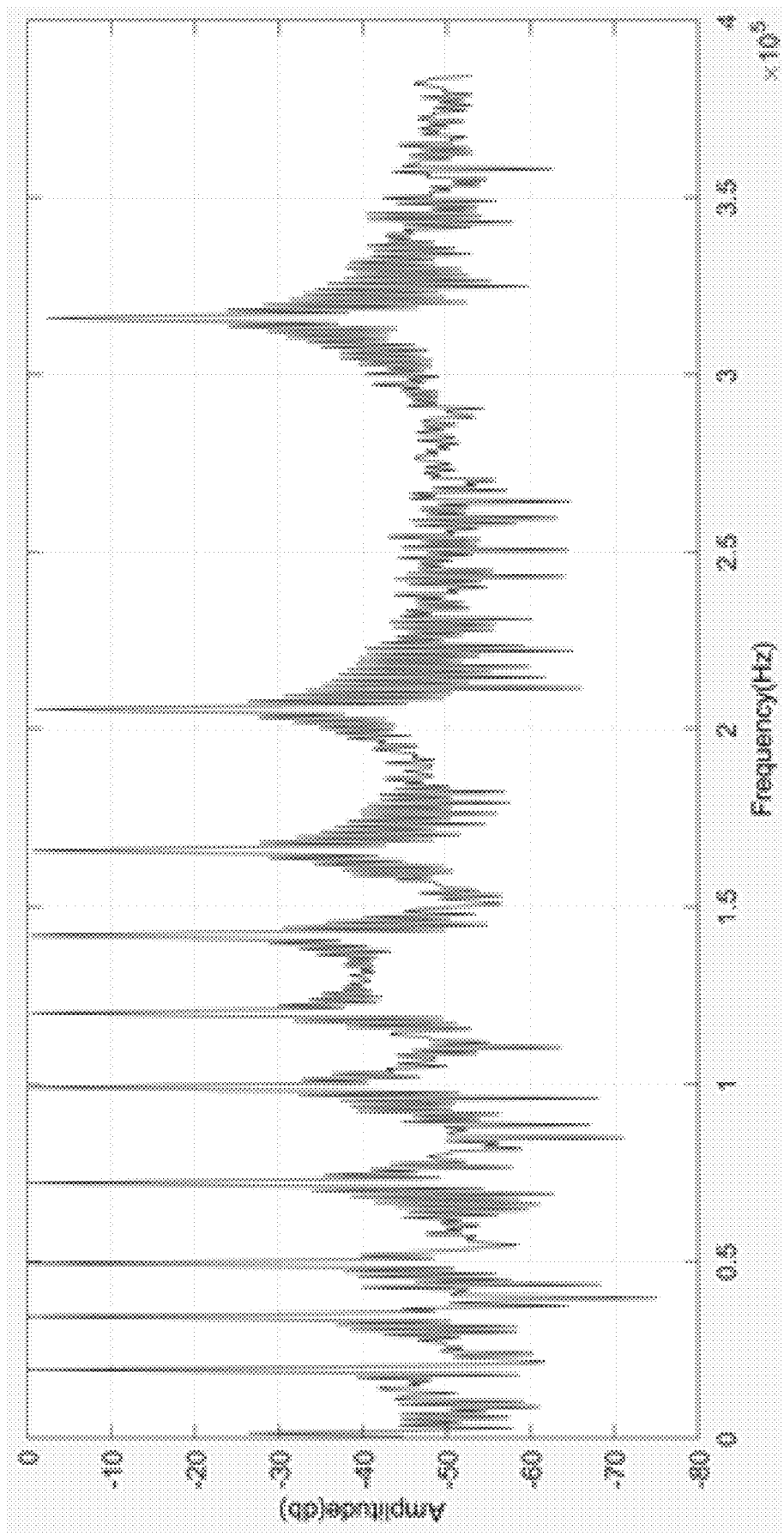
FIG. 5 is a view of a system's frequency response on a resistor according to an embodiment.

FIG. 5 shows a system's frequency response on a resistor, as a model for a human body. There are 10 major carriers of different frequencies with equal power, representing 10 frequency tones: 20.3 KHz, 35.3 KHz, 50.3 KHz, 72.9 KHz, 99.9 KHz, 120.9 KHz, 142.7 KHz, 166.8 KHz, 206.6 KHz, and 317.0 KHz. These frequencies carry the modulated information. Since the resistor will not change, frequency response is constant. Because the system is not linear, there may be different signal loss, or attenuation, at different frequencies. The signal losses or distortions caused by the system defects should be compensated or corrected before computing the RC model values and analyzing the results from humans or animals. The system phase response also needs some similar corrections.

FIGS. 6A-6B show a human or animal frequency response. The phase response (FIG. 6A) shows greater delays at higher frequencies. The amplitude response (FIG. 6B) attenuates greater at higher frequencies. These graphs show that the human or animal frequency response resembles an RC model.

FIGS. 7A-7B show a human or animal frequency response against a 2-order RC human or animal model. The measured frequency response matches very well against a 2-order RC model. Cole Model behavior is not observed here, because blood is a dominant resistance that could push the Cole central frequency much higher. The targeted tissues are modeled as a close-to linear system on a relatively narrow frequency band, like 10 KHz to 1 MHz, or on an even narrower band.

FIGS. 8A-8C show the results from a two-chamber model on the aorta measurement. FIG. 8A shows an ECG that is not a conventional 12-lead ECG. This is sufficient to show cardio-cycle timing, and so is acceptable to use, provided that R-waves are recognized. In FIG. 8B, Ra is the resistance of the aorta's chamber model. In FIG. 8C, Ca is the capacitance of the aorta's chamber model. The graphs in FIGS. 8B and 8C closely follow the heartbeats in FIG. 8A. At the end of diastole, the arteries have minimal blood reserve, and resistance is highest, while capacitance is lowest. At the end of systole, the volume of the arteries is the largest. The resistance is the smallest, while the capacitance is the largest.

FIGS. 9A-9C show the results from a two-chamber model on the aorta measurement. FIG. 9A shows an ECG that is not a conventional 12-lead ECG. This is sufficient to show cardio-cycle timing, and so is acceptable to use, provided that R-waves are recognized. In FIG. 9B, Rp is the resistance of the peripheral tissues' chamber model. In FIG. 9C, Cp is the capacitance of the peripheral tissues' chamber model. The graphs in FIGS. 9B and 9C do not show simple changes in rhythm with the heart beats. Consequently, these graphs depict an example of the kind of data which would interfere with accurate modeling, and so would be eliminated.

FIGS. 10A-10C show the results from a two-chamber model on the heart measurement. FIG. 10A shows an ECG that is not a conventional 12-lead ECG. This is sufficient to show cardio-cycle timing, and so is acceptable to use, provided that R-waves are recognized. In FIG. 10B, Rh is the resistance of the heart's chamber model. In FIG. 10C, Ch is the capacitance of heart's chamber model. The graphs in FIGS. 10B and 10C strongly follow the heart beats. At the end of diastole, the heart has the most blood, and the resistance is the smallest, while the capacitance is the largest. At the end of systole, the volume of the heart is the smallest. The resistance is the largest, while the capacitance is the smallest.

FIGS. 11A-11C show the results from a two-chamber model on the heart measurement. FIG. 11A shows an ECG that is not a conventional 12-lead ECG. This is sufficient to show cardio-cycle timing, and so is acceptable to use, provided that R-waves are recognized. In FIG. 11B, Rp is the resistance of the peripheral tissues' chamber model. In FIG. 11C, Cp is the capacitance of the peripheral tissues' chamber model. The graphs of FIGS. 11B and 11C do not show clear changes in rhythm with the heart beats.

Figures 12A, 12B, 12C, 13A, 13B, 13C:
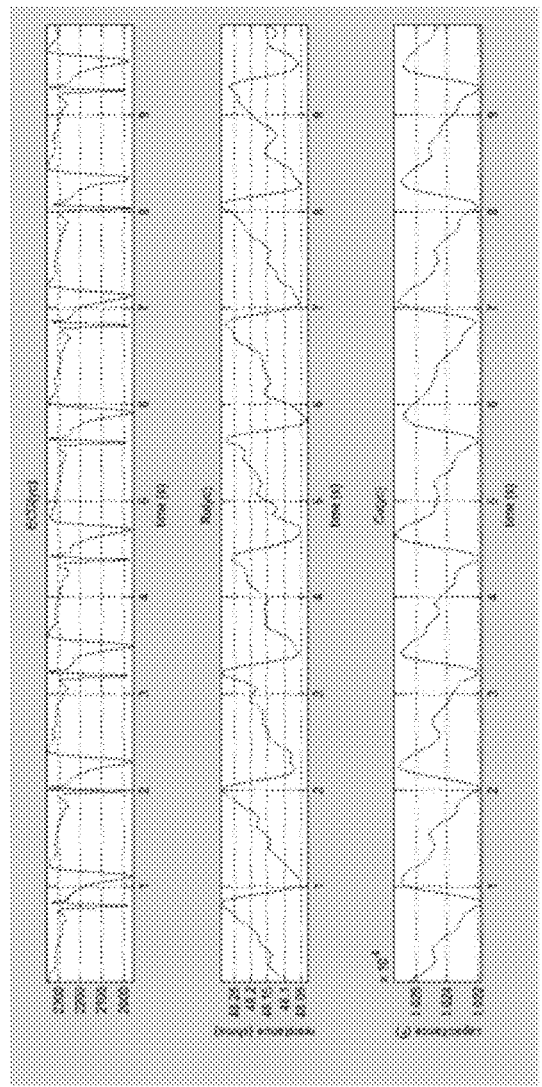
FIGS. 12A-12C are graphs of artery results from a two-chamber model on the chest measurement according to an embodiment.
FIGS. 13A-13C are graphs of peripheral results from a two-chamber model on the chest measurement according to an embodiment.

FIGS. 12A-12C show the results from a two-chamber model on the upper chest (thorax) measurement. FIG. 12A shows an ECG that is not a conventional 12-lead ECG. This is sufficient to show cardio-cycle timing, and so is acceptable to use, provided that R-waves are recognized. In FIG. 12B, Ru is the resistance of the upper chest's chamber model, which includes thoracic arteries and the heart. In FIG. 12C, Cu is the capacitance of the upper chest's chamber model. The graphs in FIGS. 12B and 12C strongly follow the heart beats. Before ventricles compress, the arteries have the lowest blood reserve. The resistance is the highest, while the capacitance is the lowest. At the end of systole, the volume of arteries is the largest. The resistance is the smallest, while the capacitance is the largest.

FIGS. 13A-13C show the results from a two-chamber model on the upper chest measurement. FIG. 13A shows an ECG that is not a conventional 12-lead ECG. This is sufficient to show cardio-cycle timing, and so is acceptable to use, provided that R-waves are recognized. In FIG. 13B, Rp is the resistance of the peripheral tissues' chamber model. In FIG. 13C, Cp is the capacitance of the peripheral tissues' chamber model. The graphs in FIGS. 13B and 13C are not changing as clearly with the heart beats as is the case with the upper-chest chamber model.

FIGS. 14A-14C show the results from a two-chamber model on the right lung measurement. FIG. 14A shows an ECG that is not a conventional 12-lead ECG. This is sufficient to show cardio-cycle timing, and so is acceptable to use, provided that R-waves are recognized. In FIG. 14B, "R right lung" is the resistance of the right lung's artery/vein chamber model. In FIG. 14C, "C right lung" is the capacitance of the right lung's artery/vein chamber model. The graphs in FIGS. 14B and 14C vary closely with the heart beats.

FIGS. 15A-15C show the results from a two-chamber model on the right lung measurement. FIG. 15A shows an ECG that is not a conventional 12-lead ECG. This is sufficient to show cardio-cycle timing, and so is acceptable to use, provided that R-waves are recognized. In FIG. 15B, Rp is the resistance of the right lung's peripheral tissues' chamber model. In FIG. 15C, Cp is the capacitance of the right lung's peripheral tissues' chamber model. The graphs of FIGS. 15B and 15C also are changing closely with the heart beats.

FIGS. 16A-16C show the results from a two-chamber model on the left lung measurement. FIG. 16A shows an ECG that is not a conventional 12-lead ECG. This is sufficient to show cardio-cycle timing, and so is acceptable to use, provided that R-waves are recognized. In FIG. 16B, "R left lung" is the resistance of the left lung's artery/vein chamber model. In FIG. 16C, "C left lung" is the capacitance of the left lung's artery/vein chamber model. Since the left lung have arteries and veins and the heart, the model is more complicated than just a simple two-chamber model. The graphs look different from others, but the graphs of FIGS. 16B and 16C still appear to change in some kind of rhythm with the heart beats.

FIGS. 17A-17C show the results from a two-chamber model on the left lung measurement. FIG. 17A shows an ECG that is not a conventional 12-lead ECG. This is sufficient to show cardio-cycle timing, and so is acceptable to use, provided that R-waves are recognized. In FIG. 17B, Rp is the resistance of the left lung's peripheral tissues' chamber model. In FIG. 17C, Cp is the capacitance of the left lung's peripheral tissues' chamber model. The graphs in FIGS. 17B and 17C appear to be changing closely with the heartbeats, a different result from what is shown in other Figures.

As described herein, embodiments of the present invention provide a method and system to detect tissues' characteristic information in humans and animals by applying multiple AC currents of different frequencies simultaneously to a human or animal body. After the modulated voltage signals are received, they are demodulated. Information about both the cardiovascular system and from surrounding tissues then is extracted from the sub-carriers of specified frequencies. System identification or channel estimation procedures separate the information from the cardiovascular circulation system and the surrounding tissues. Resistance and capacitance of the cardiovascular system and surrounding tissues are calculated, separately, using the computed resistance and capacitance to represent the states of body fluid and cardiovascular circulation. As a result, relevant state information is obtained accurately and reliably to enable the measurements of targeted tissues and thus acquire health states.

While the foregoing specification describes embodiments, various changes and modifications within the scope of the invention will be apparent to ordinarily skilled artisans without departing from the scope of the present invention. Accordingly, the scope of the invention is to be determined according to the scope of the following claims.

What is claimed is:

1. A non-invasive method to detect characteristic information of internal body tissues, to capture changes of bodily fluid, blood flow, and cardiovascular circulation, the method comprising:
    generating multiple alternating currents of different frequencies simultaneously by generating multiple alternating currents of different frequencies from a frequency domain to a time domain using digital signal processing technologies, wherein the generated multiple alternating currents of different frequencies are periodic;
    transmitting the generated multiple alternating currents of different frequencies simultaneously into a human or animal body to produce multiple alternating voltage signals;
    receiving the alternating voltage signals, as modulated by tissues' changes in the human or animal body;
    amplifying and digitizing the received alternating voltage signals into digital signals;
    pre-processing the digital signals, the pre-processing further comprising demodulating, filtering, and separating the digital signals, wherein the separating the digital signals comprises separating resistance and capacitance values of peripheral tissues from resistance and capacitance values of targeted tissues calculated from complex impedance of multiple frequencies; and
    estimating states of targeted tissues.

2. The method according to claim 1, wherein the receiving the alternating voltage signals comprises determining a period of transmitted alternating currents, and synchronizing the received alternating voltage signals every period.

3. The method according to claim 1, further comprising calculating the resistance and capacitance values of the targeted tissues and the resistance and capacitance values of the peripheral tissues through system identification or channel estimation procedures.

4. The method according to claim 3, wherein the system identification or channel estimation procedures comprise multi-chamber modeling using the resistance and capacitance values, and wherein each chamber is modeled by a parallel resistance and capacitance, and wherein multiple chambers are connected serially, or in parallel.

5. The method according to claim 4, wherein the multi-chamber modeling comprises two-chamber modeling, and connecting tissues are between electrodes and the targeted tissues.

6. The method according to claim 1, wherein the frequency range of the generated multiple alternating currents is from 10 KHz to 1 MHz.

7. The method according to claim 1, wherein the generating multiple alternating currents of different frequencies simultaneously comprises summing multiple alternating currents of different frequencies in a time domain using digital signal processing technologies, wherein the multiple alternating currents of different frequencies are periodic.

8. A system to implement the method of claim 1, wherein the system comprises a terminal and at least one processor, wherein the terminal comprises:
    a generator to generate the multiple alternating currents of different frequencies;
    at least one transducer to transfer the generated multiple alternating currents of different frequencies into a human body or animal body, and receive the alternating voltage signals of different frequencies modulated by the tissues' changes in the human or animal body;
    at least one amplifier to amplify the received alternating voltage signals of different frequencies as amplified signals, and at least one analog to digital converter to digitize the amplified signals into digital signals; and
    a pre-processing module to pre-process the digital signals by demodulating, filtering, and separating the digital signals;
    wherein the at least one processor is configured to estimate states of targeted tissues.

9. The system according to claim 8, further comprising at least one math accelerator configured to calculate resistance and capacitance values of the digital signals.

10. The system according to claim 9, wherein the pre-processing module is configured to determine a period of transmitted alternating currents and to synchronize the received alternating voltage signals every period.

11. The system according to claim 10, wherein the at least one transducer is configured to sample multiple signals alternatively or simultaneously from different segments of the human or animal body.

12. The system according to claim 11, wherein the pre-processing module is configured to separate the peripheral tissues' resistance and capacitance from the targeted tissues' resistance and capacitance calculated from a complex impedance of multiple frequencies.

13. The system according to claim 11, wherein the at least one math accelerator is configured to calculate resistance and capacitance values of the targeted tissues and peripheral tissues through system identification or channel estimation procedures.

14. The system according to claim 13, wherein each processor is configured to model a multi-chamber equivalent circuitry through the resistance and capacitance values of the targeted tissues or the peripheral tissues, and each chamber consists of a parallel resistance and capacitance, and multiple chambers are connected serially, or in parallel.

15. The system according to claim 8, further comprising a database to store results from the at least one processor, the at least one processor configured to retrieve the results.

16. The system according to claim 15, wherein the database enables monitoring of the system in a real-time mode or an offline mode.

17. The system according to claim 8, wherein the generator is configured to sum multiple alternating currents of different frequencies in a time domain using digital signal processing technologies, wherein the multiple alternating currents of different frequencies are periodic.

* * * * *